United States Patent [19]
Dyson et al.

[11] Patent Number: 6,073,045
[45] Date of Patent: Jun. 6, 2000

[54] APPARATUS FOR ULTRASONIC TISSUE INVESTIGATION

[75] Inventors: Mary Dyson, Berkhamsted; Hugh Lewis, Didcot; Stephen Robert Young, Petts Wood, all of United Kingdom; John Andrew Lynch, San Francisco, Calif.; Walter Raymond Dyson deceased, late of, Berkhamsted, United Kingdom, by Mary Dyson, Legal Represenative

[73] Assignee: Longport Incorporated, Swathmore, Pa.

[21] Appl. No.: 08/894,791

[22] PCT Filed: Mar. 11, 1996

[86] PCT No.: PCT/GB96/00566

§ 371 Date: Feb. 9, 1998

§ 102(e) Date: Feb. 9, 1998

[87] PCT Pub. No.: WO96/28096

PCT Pub. Date: Sep. 19, 1996

[30] Foreign Application Priority Data

Mar. 9, 1995 [GB] United Kingdom .................. 9504751

[51] Int. Cl.[7] ...................................................... A61B 8/00
[52] U.S. Cl. ............................. 600/433; 600/447; 73/643
[58] Field of Search .................................. 6000/443, 444, 6000/447, 459, 462; 364/413.01; 73/602, 625, 643, 627, 629

[56] References Cited

U.S. PATENT DOCUMENTS 4,858,124  8/1989  Lizzi et al. ........................ 364/413.01
5,115,814  5/1992  Griffith et al. .......................... 600/462
5,394,750  3/1995  Matzuk ..................................... 73/629
5,601,082  2/1997  Barlow et al. .......................... 600/443
5,721,379  2/1998  Palmer et al. ............................ 73/643

FOREIGN PATENT DOCUMENTS 0 219 128  4/1987  European Pat. Off. .

OTHER PUBLICATIONS (French) Berson, et al., "Imagerie acoustique a haute resolution Applications en dermatologie," *L'Onde Electrique*, Mar./Apr. 1999, vol. 72, No. 2, pp. 31–35.

Turnbull, et al., "Ultrasound Backscatter Microscope for Skin Imaging," 1993 *Ultrasonics Symposium*, published Oct. 31, 1993, pp. 985–988.

*Primary Examiner*—Marvin M. Lateef
*Assistant Examiner*—Ali M. Imam
*Attorney, Agent, or Firm*—Knoble & Yoshida LLC

[57] ABSTRACT

The apparatus for ultrasonic tissue investigation comprises an ultrasonic transducer (1) adapted to emit pulsed emissions into tissue and means (2) to move the transducer to scan an area of tissue to be investigated. Signals reflected from interfaces between acoustically different tissue components are received and converted into a representation of the tissue, which may be visually displayed. The emissions of ultrasonic radiation are so pulsed that each pulse has a very rapid fall back period, enabling better discrimination. Interpretation of the images may be facilitated by use of such techniques as fractal analysis.

21 Claims, 9 Drawing Sheets

APPARATUS FOR ULTRASONIC TISSUE INVESTIGATION

The present invention relates to an apparatus for an investigation of tissue based on the emission and reception of ultrasound.

It is known to use ultrasound to carry out investigations of the human body and other animal bodies. In these cases, an ultrasonic transducer is linked acoustically to the skin of a patient, optionally with the introduction of an appropriate coupling and lubricating medium. Ultrasonic pulses transmitted into the patient are then reflected from reflecting surfaces at interfaces between the various layers of tissue within the patient. The reflected pulses are received by the transducer and signals representative of the pulses are generated and combined by appropriate computing means to enable a visual representation of the zone of treatment of the patient to be recreated.

One example of the use of such techniques is ultrasonic scanning of a foetus in a pregnant mothers womb.

Human and other animal tissues are arranged in layers from superficial to deep usually comprising the outermost layer of epidermis, followed by papillary and reticular layers of dermis, beneath which lies a layer of fat, and then other tissues such as tendon, ligament, muscle and bone. At each of the interfaces between these various layers, a proportion of the ultrasonic input will be reflected and can be received to generate a visually identifiable picture of the condition at any one particular interface. This enables and aids diagnosis of any disorder of the skin or underlying tissue.

However, presently available techniques cannot always give a clear enough view of any likely problem, and it is therefore an object of the present invention to provide an apparatus which will give an improved representation of the condition of a patient at a desired location within or beneath the skin.

According to a first aspect of the present invention there is provided an apparatus for ultrasonic tissue investigation comprising ultrasonic transducer means adapted to emit pulsed emissions into tissue, means so to move said transducer means as to scan an area of tissue to be investigated, means to receive signals reflected from interfaces between tissue layers, means to convert said received signals into a visual image of the tissue, and means to display said visual image, wherein said emissions of ultrasonic radiation are so pulsed that each pulse has a very rapid fall back period.

Preferably there are provided means to analyse the data from which these images are produced.

Preferably, the received signals are split into positive and negative part signals, each of which is separately amplified by log compressor means, with the amplified signals being recombined to give an input to said means to convert said recombined signals into a visual image.

The means to move said ultrasonic transducer may be a stepper motor adapted to move said ultrasonic transducer within an area having a travel of up to approximately 15 mm, using a transducer of diameter up to approximately 6 mm.

Each scan of the area may involve a plurality of pulses, having a pulse repetition frequency in the region of 1 ms, each pulse being of duration less than 50 ns.

According to a second aspect of the present invention there is provided a method of tissue investigation comprising scanning an area of tissue using an apparatus as described above.

An embodiment of the present invention will now be more particularly described by way of example, and with reference to the accompanying drawings, in which.

Figure 1:
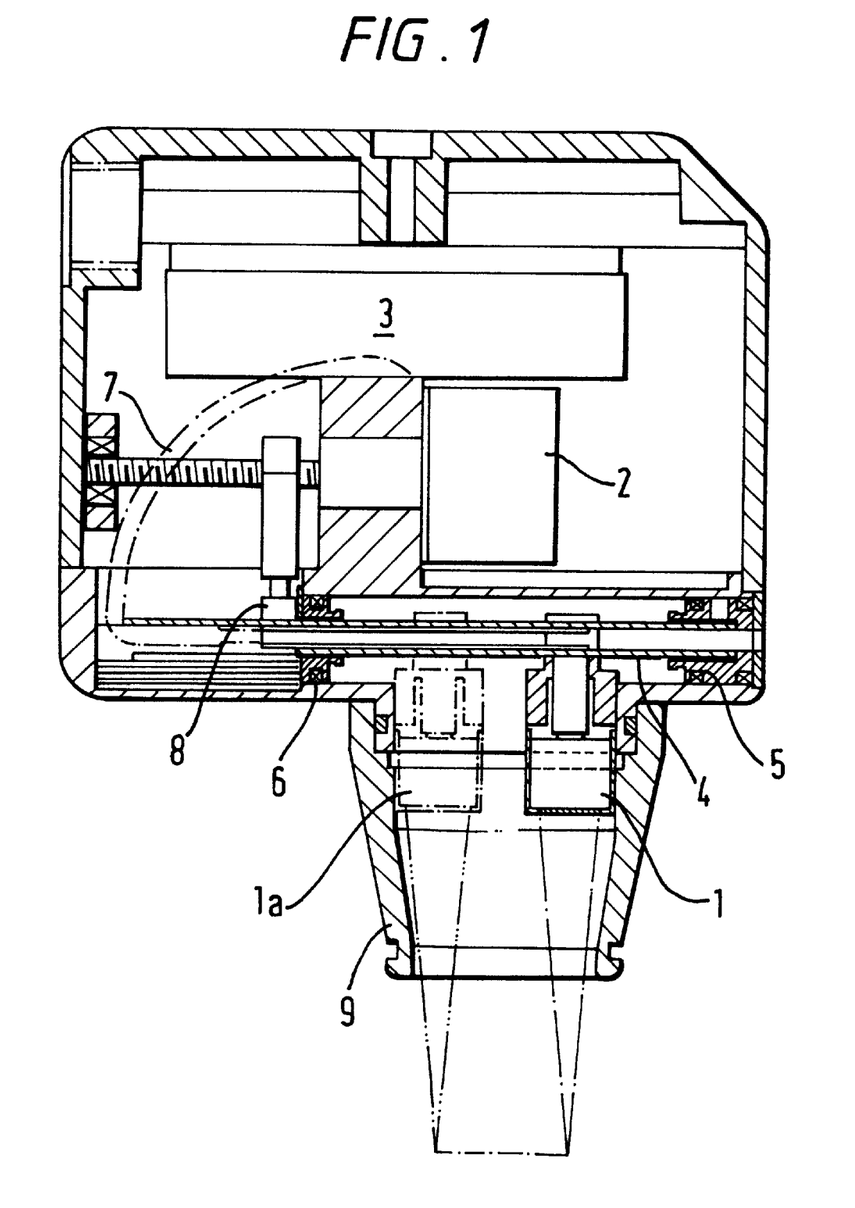
FIG. 1 is a cross sectional view of a probe head for use in the present invention.

Referring now to the drawings, FIG. 1 shows an apparatus for application to an area of skin, of a patient or hide. The apparatus comprises a transducer 1, which may be moved by means of a stepper motor 2 to scan an area of tissue on or under that particular area of skin. The motor 2 drives shaft 4, which is supported between an external shift bearing 5 and an internal shaft bearing 6, and the transducer 1 is movable between positions 1 and 1a as shown in FIG. 1.

The transducer is driven along the shaft by means of flexible drive 7 although connection may also be made through link arm 8.

The transducer 1, housed within cone 9, has preferably a piezoelectric polymer element capable of emitting a single cycle pulse at a frequency of between 10 and 50 MHz. The preferred centre frequency is in the region of 20 MHz and, as will be described below the probe transducer is activated at a high voltage, and the system is adapted to cause an ultra fast rise and fall time pulse. The sharp signals given thereby enable a better reception of the reflected signals.

The control electronics of the system are housed in area 3 and are described in more detail below. Of these, the probe electronics contain a pulse generator for energising the ultrasound transducer and a preamplifier for the returning signal. The time gain compensator and motor control unit contains the main signal amplifier and the control and drive electronics for the probe motor. This may be connected to a compatible computer along with an analogue to digital converter board.

Figures 2, 2A:
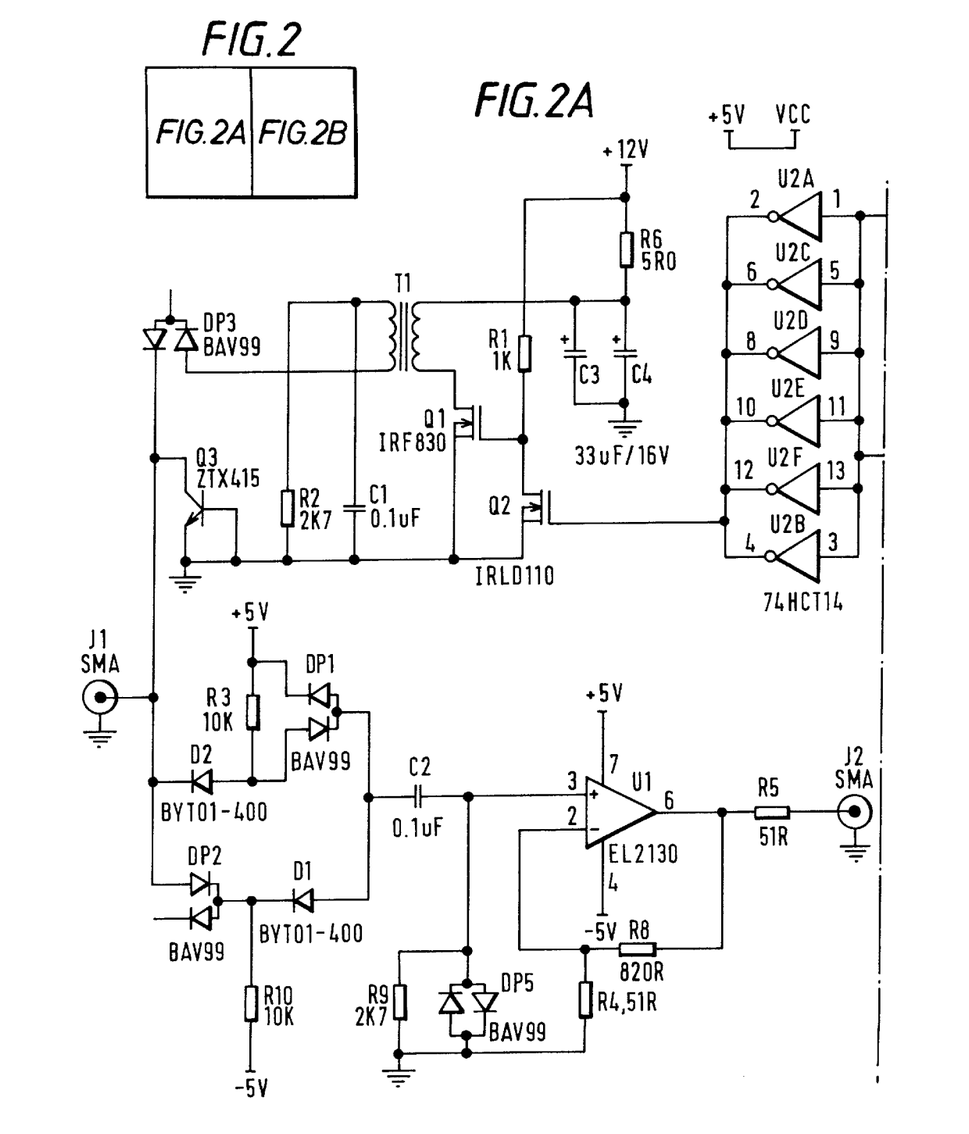
FIG. 2 is a diagram of the circuit for the probe pulser and preamplifier of the present invention.
Figure 2B:
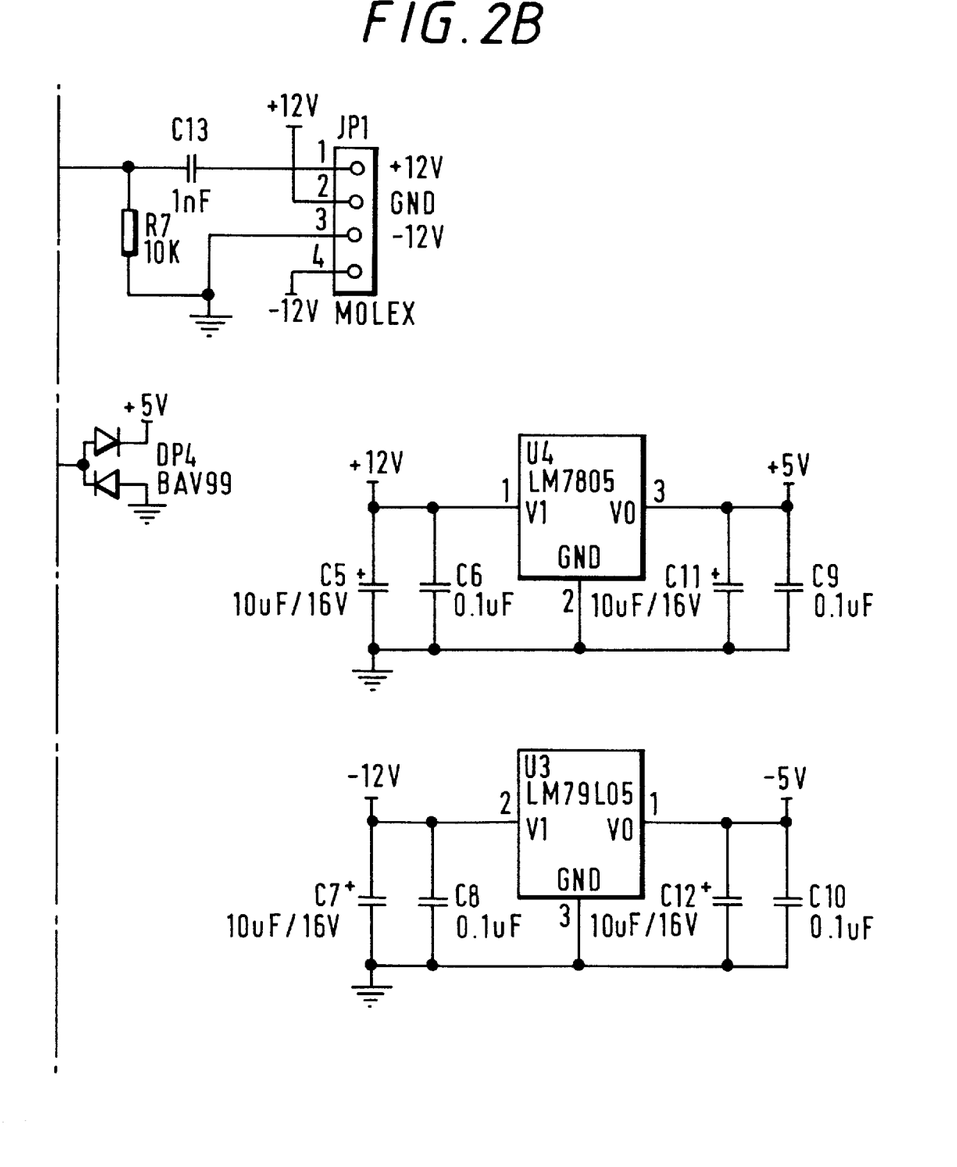

In the probe electronics there are two parts. Firstly the pulser, which generates an ultra fast signal of rise and fall time (>30 kV/$\mu$s) very short duration (<20 ns) high voltage pulse (>300V). The pulse is produced from a single low voltage (+12 volt) supply to the board. The pulse is created by the back emf of a small inductor acting as an impedance transformer with an avalanche transistor to limit the pulse duration and to produce an ultra fast fall time for the pulse.

Power is supplied to the circuit through pins 2 and 3 of JPI. Pulse triggering is generated by a 3 $\mu$s 5 volt positive supplied to pin 1 of JPI. This causes the inputs to U2 of the 74HCT14 hex inverting Schmitt triggered buffer to go high for 3 $\mu$s. The turn on speed of Q1 is limited by R1 and the gate capacitance of Q1. This prevents a significant pulse from the in-rush current into T1, which saturates within 3 $\mu$s. On the falling edge of the trigger pulse the outputs of U2 go high turning Q2 on quickly which turns off Q1 in less than 10 ns. This causes a back emf pulse of in excess of 600 volts to be generated across T1. This is stepped down to a 300 volt pulse at the output of T1. The diodes in DP3 conduct and the pulse is fed to the transducer connected to J1. When the output pulse voltage reaches greater than 300 volts Q3 breaks down in an avalanche shorting transformer and limits the pulse duration.

In this respect there is provided a preamplifier with input protection, which consists of a standard current mode opamp with the input protected by a diode bridge. This amplifier has a voltage gain of 17 (12.3 dB).

The received signal, having been preamplified, is fed to a time gain compensation circuit to allow for attenuation through the various layers of tissue being investigated.

Figures 3, 3A:
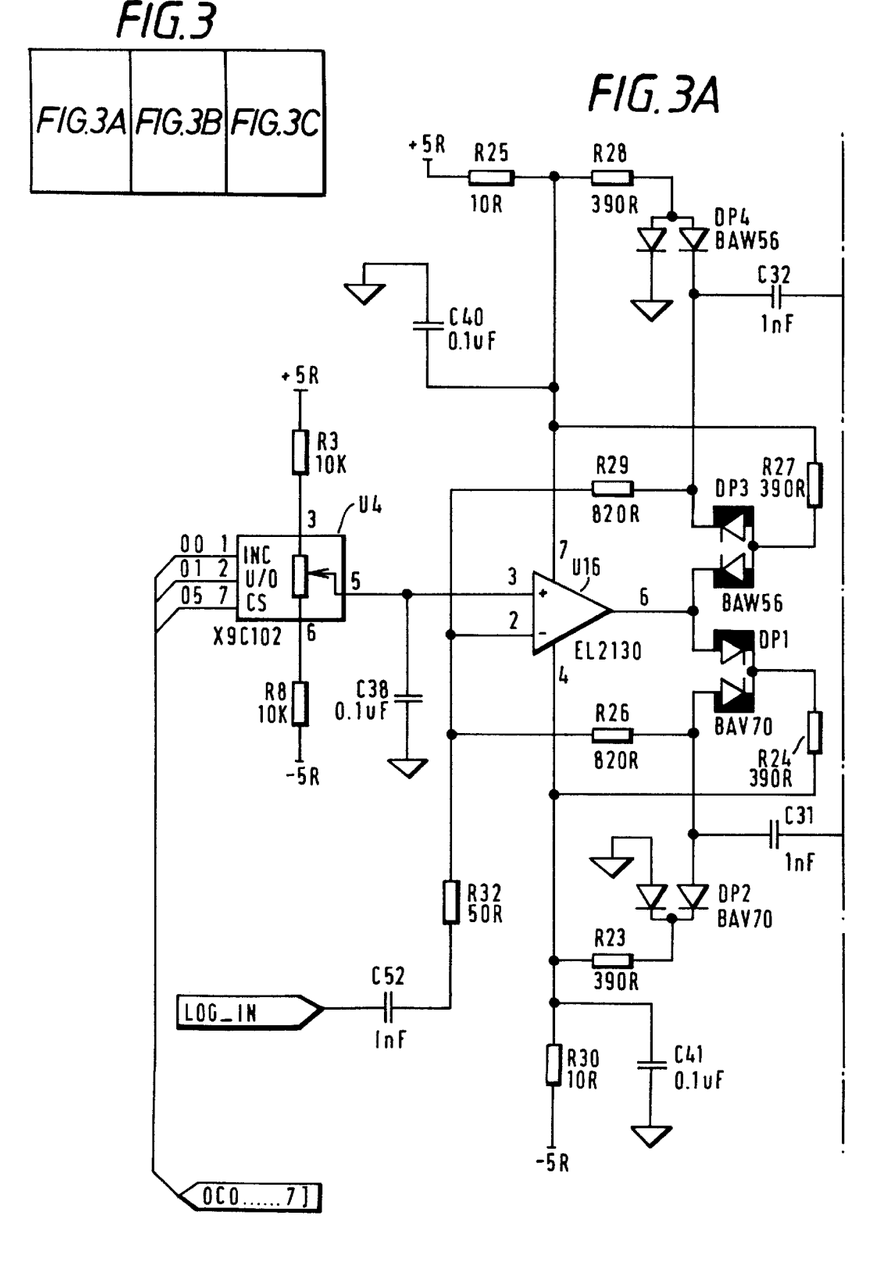
FIG. 3 is a circuit diagram for the log amplifier system of the present invention.
Figure 3B:
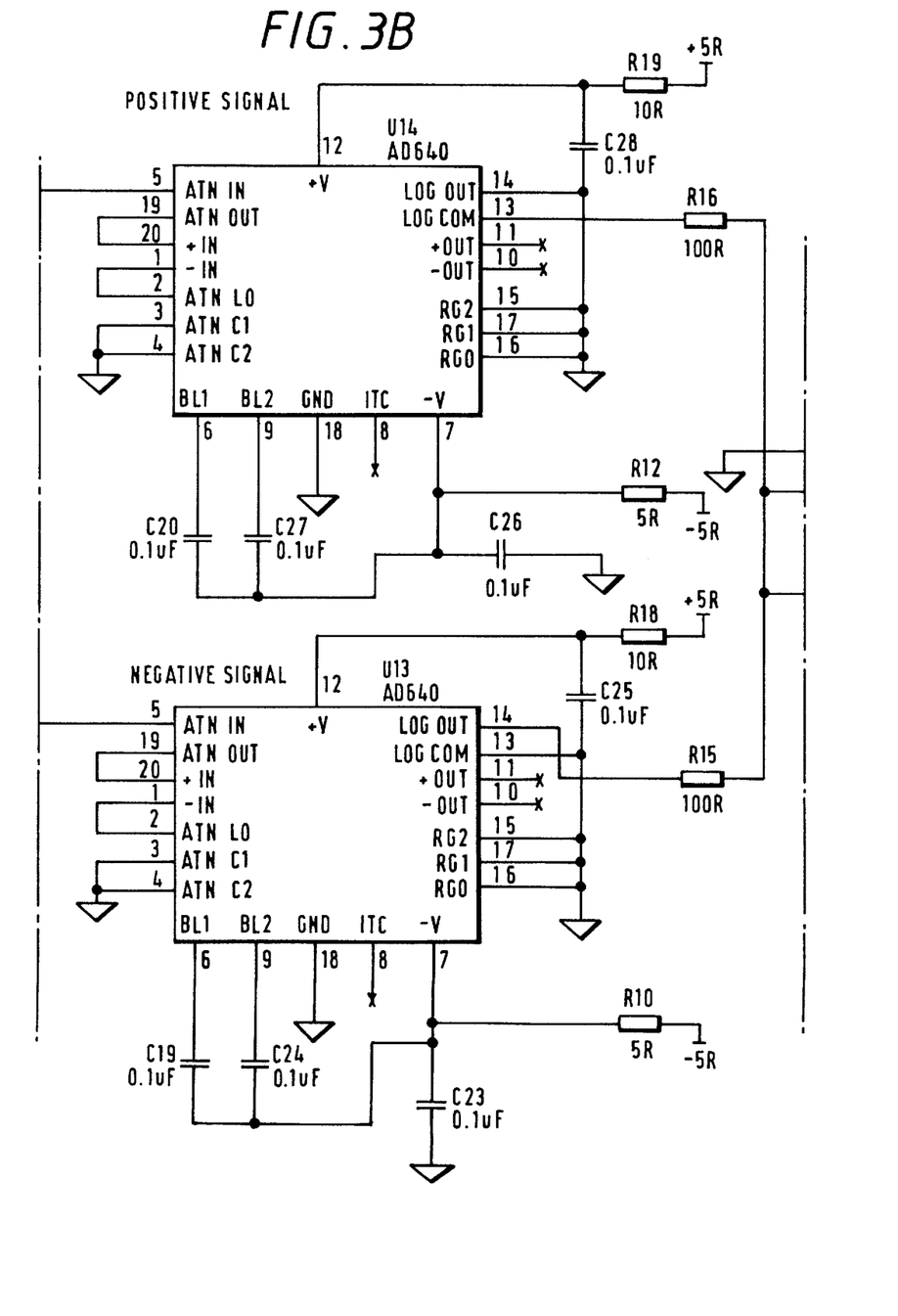
Figure 3C:
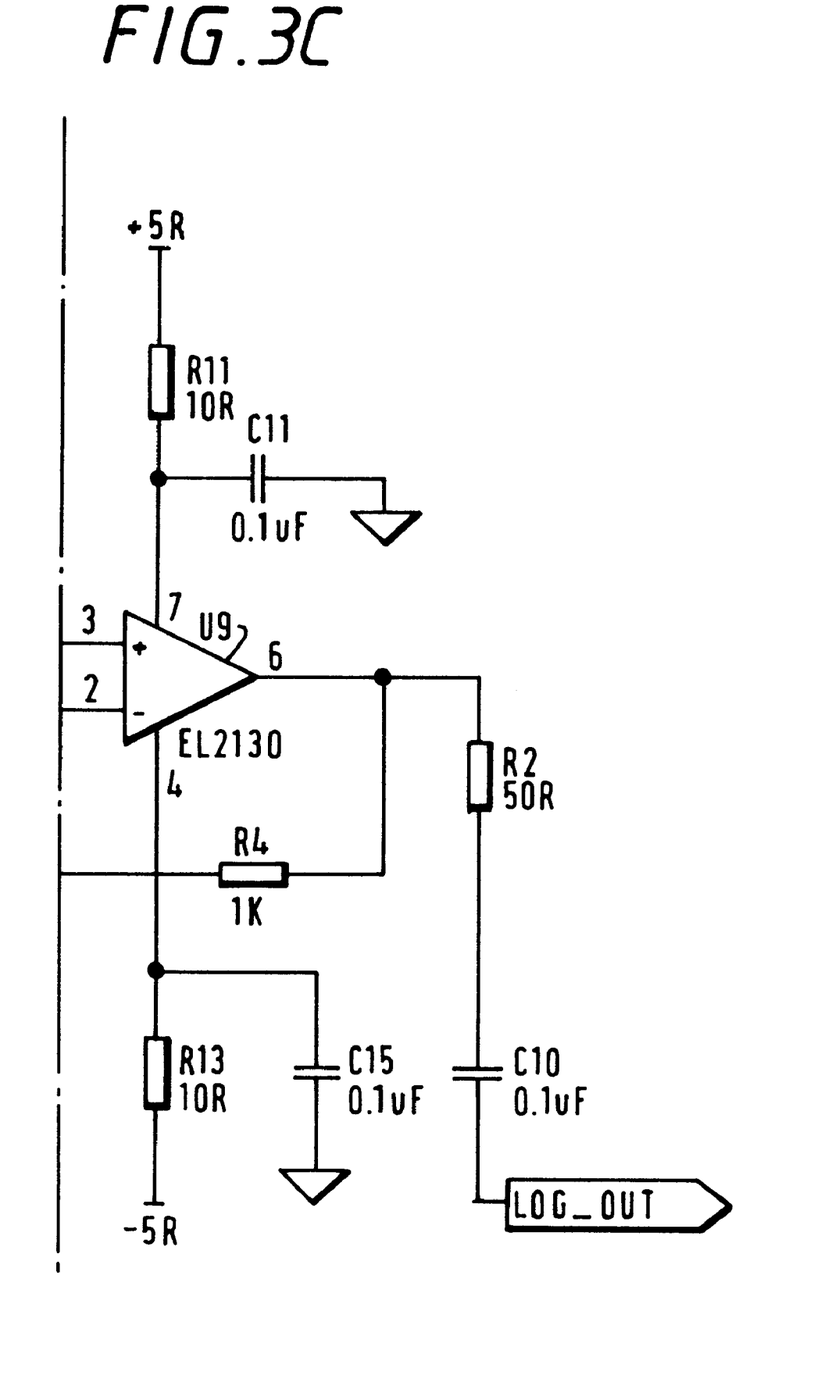
Figure 4:
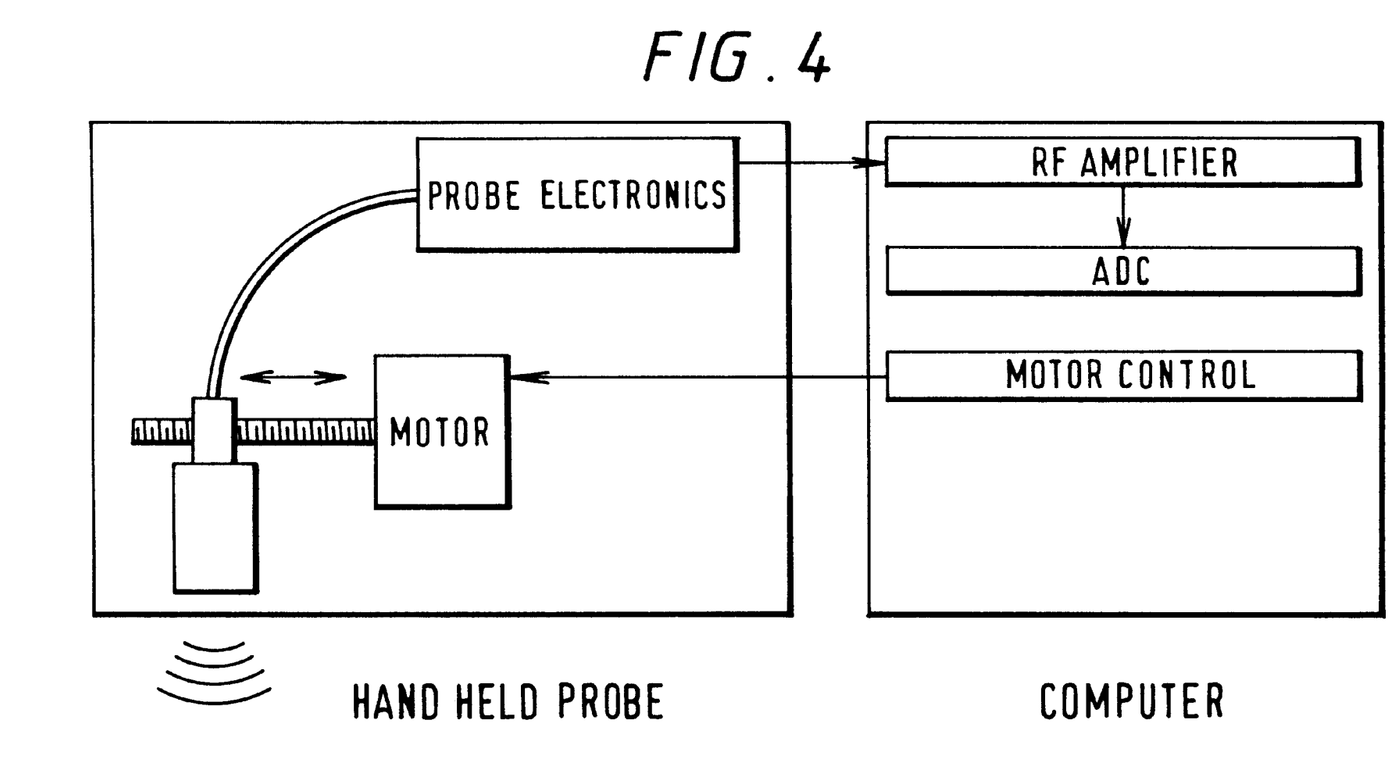
FIG. 4 shows the system in a schematic form.
Figure 5:
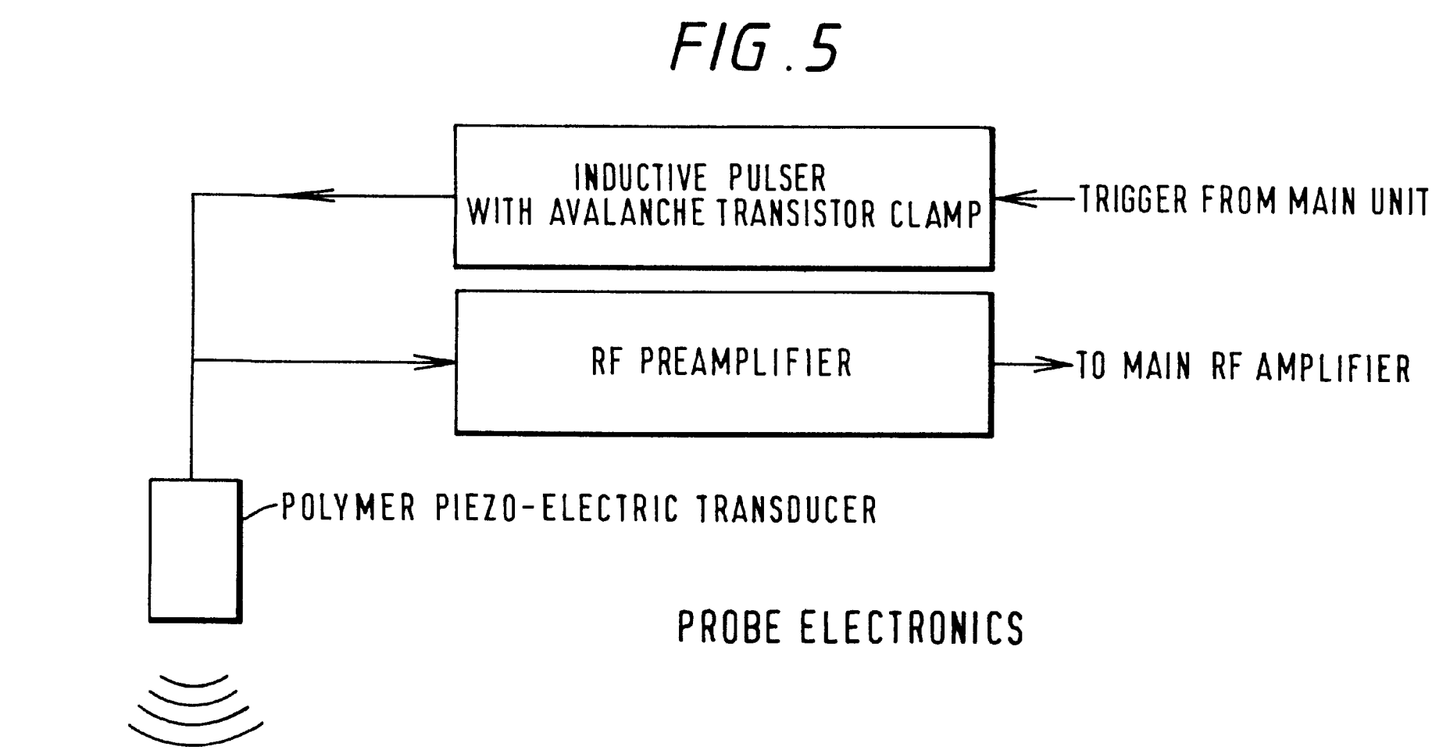
FIG. 5 shows schematically the electronic systems of the probe.
Figure 6:
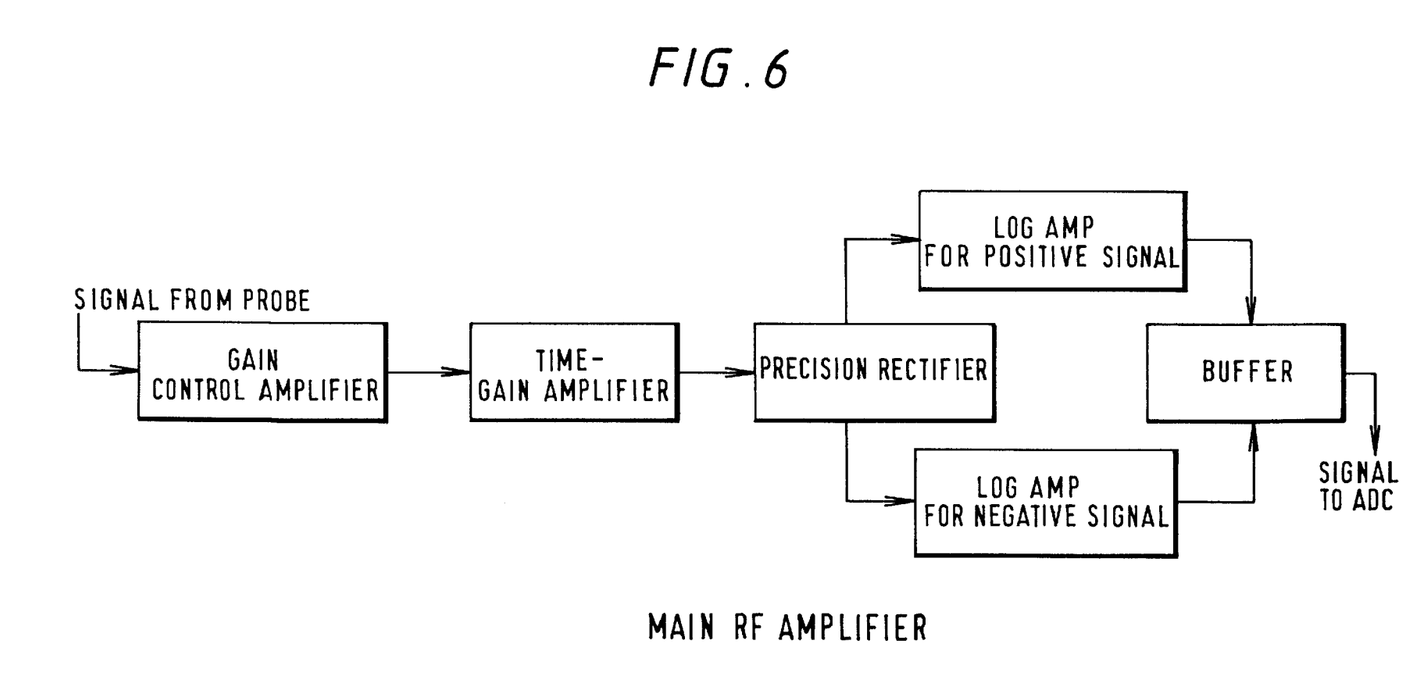
FIG. 6 shows schematically the electronic systems of the main RF amplifier.

An amplifier consists of five stages. The first stage is a variable gain amplifier with a −10 dB to +30 dB control. This acts as overall gain control for the system. The second stage is a variable gain amplifier and ramp generator with a 0 to +30 dB control range that is ramped at a controlled rate and acts as the time gain compensation. The third stage is a precision rectifier that splits the signal into the positive and negative parts of the signal, and for the fourth stage, a log compressor consisting of two 50 dB log amps. The output of these two log amps is recombined in the fifth stage and buffered to give a 50 ohm output for input to the analogue/digital converter.

Secondly, a motor control comprises a bipolar stepper motor drive using MOSFET transistors with phase sequencing provided by a specially programmed PAL. The step rate and step count is controlled by the host computer through an industrial standard 8254 counter/timer IC.

By keeping apart the positive and negative parts of the return signal, and then combining them after amplification it has been found that the signal has an improved range and discrimination when transferred to an analogue digital converter and thence to the computing means and visual display means.

Value can be added to the visual display by subjecting the returned signals either to a process of fractal analysis, wavelet analysis or a fast Fourier transform.

Fractal analysis comprises representing the region of interest of the skin and underlying tissue as a three dimensional landscape, with lateral and axial dimensions on a horizontal plane and the intensity of the image (0–256) on a vertical axis. The area of landscape can then be mapped using flat disc shaped structuring elements with no height in a grey scale dimension and using techniques of mathematical morphology, the surface area of the image can be measured at different resolutions by removing features of less than a particular size. According to the method, this can be performed for resolutions between 1 pixel up to 20 pixels. At any given resolution, the rate of change of the surface area with respect to resolution is related to the estimated fractal dimension at that resolution. The set of estimated fractal dimensions up to resolutions of 20 pixels defines the fractal signature.

Experiments show that, in using this system, various areas of tissue have a distinctive signature. For example, signatures from forehead tissue and regions of the hand lie particularly close together throughout pixel size, especially in the range of 2–5 pixels, peaking with fractal dimensions between 3.5 and 4.0 at 5 pixels. Other parts of the body gave different signatures, for example a scan of heel tissue peaks at 9 pixels with a fractal dimension of 3.2.

Similar experiments using fast Fourier transforms (FFTs) have shown that the heel sample shows the lowest overall curve amplitude, whilst the samples from equivalent tissues of the hand show a remarkable similarity in curved shape and size, from whichever part of the hand the samples were taken. Samples taken from forehead tissue show the greatest amplitude at the first peak, with the second peak lower, showing the prevalence of narrow bands. Samples from hand and heel tissues show second peaks larger than the first ones, showing the prevalence of wide bands.

It is thought that fractal analysis will give different signatures for normal and damaged tissues, and the information can be stored for use as a comparison in all future studies. A databank built up in this way would be able to give more immediate attention to any abnormalities in the tissue being examined.

Apparatus embodying the invention will find use in identifying and diagnosing tumours. injuries and any other abnormal condition up to depth of 3–5 cm below the skill surface being investigated. Such noninvasive investigation is obviously a benefit to the patient and the apparatus provides a means of carrying out such investigation quickly, and with the advantage of giving clear images of any problem which may be encountered within the tissue surveyed.

One further use of the invention is in the testing of hides, sheepskins, and other materials used for commercial purposes such as clothing or footwear. In this case, the value of the hide will depend upon its surface perfection. This is not easy to see until the hair (or wool or the like) has been removed. The apparatus of the present invention can be used to scan a hide from an "inside" (deep) surface thereof and determine whether imperfections are likely to appear on the opposite "outside" surface once the hair has been removed.

What is claimed is:

1. An apparatus for ultrasonic tissue investigation comprising:

ultrasonic transducer means adapted to emit pulsed emissions into tissue;

means so to move said transducer means as to scan an area of tissue to be investigated;

means to receive pulses reflected from interfaces between tissue components; and means to convert said received pulses into a visual image of the tissue and means to display said visual image, and wherein said ultrasonic transducer means is constructed and arranged so that said emissions of ultrasonic radiation are so pulsed that each pulse has a very rapid fall back period, said fall back period having a fall back rate that is greater than 30 kV/$\mu$s.

2. An apparatus according to claim 1, wherein the received signals are split into positive and negative part signals, each of which is separately amplified, optionally by log compressor means, with the amplified signals being recombined to give an input to said means to convert said recombined signals into a visual image.

3. An apparatus as claimed in either claim 1 or claim 2, wherein said signal converting means comprises additionally analysis means to analyze said signals.

4. An apparatus as claimed in claim 3, wherein said analysis means comprises means to perform fractal analysis, wavelet analysis or a fast Fourier transform.

5. An apparatus according to claim 1, wherein the means to move said ultrasonic transducer is a stepper motor, preferably adapted to move said ultrasonic transducer within an area having a travel of up to 15 mm.

6. An apparatus according to claim 5, wherein the transducer element has a diameter in the region of up to 6 mm.

7. An apparatus according to claim 1, wherein each scan of said area of tissue involves a plurality of pulses, having a pulse repetition frequency in the region of 1 KHz, each pulse being of duration less than 50 ns.

8. A method of tissue investigation, comprising steps of:

(a) moving an ultrasonic transducer of the type that is adapted to pulse emissions into tissue over an area of tissue to be investigated;

(b) scanning an area of tissue using the transducer;

(c) receiving signals reflected from interfaces between tissue layers within said area;

(d) converting said received signals into a visual image of the tissue; and (e) displaying said visual image, and wherein step (b) is conducted so that said emissions of ultrasonic radiation are so pulsed that each pulse has a very rapid fail back period said fall back period having a fall back rate that is greater than 30 kV/μs.

9. A method of tissue investigation comprising:

(a) scanning an area/volume of tissue to be investigated by a moving ultrasonic transducer means emitting pulsed emissions, each having a very rapid fall back period said fall back period having a fall back rate that is greater than 30 kV/μs, into said tissue;

(b) receiving signals reflected from tissue component interfaces converting said received signals into a visual image of the tissue and displaying said visual image.

10. A method as claimed in either claim 8 or claim 9, further comprising the step of analyzing said signals, optionally by fractal analysis, wavelet analysis or fast Fourier transform.

11. A method of tissue investigation, as claimed in claim 9, wherein the tissue is a hide, sheepskin or other usable animal product.

12. A method as claimed in claim 11, wherein the scanning means is applied to an interior (deep) side of the hide, sheepskin or other usably animal tissue to defect imperfections on a surface thereof which is obscured by hair, fur, wool or other keratinous material.

13. A method of tissue investigation according to claim 9, further comprising storing said received signals, carrying out the method on an area of tissue, and comparing the signals received with those stored for a comparative area of tissue.

14. An apparatus for performing an ultrasonic investigation of a subject, comprising:

emitting means for emitting an ultrasonic pulse into a subject, said emitting means being constructed and arranged to utilize a combination of inductive and avalanche elements to generate an electrical pulse and a transducer for converting the electrical pulse into an ultrasonic pulse;

receiving means for receiving a portion of said ultrasonic pulse that has passed through at least a portion of the subject; and analyzing means for analyzing data that has been received by said receiving means.

15. An apparatus according to claim 14, wherein said emitting means utilizes an inductor to create a pulse, and wherein said emitting means further comprises an avalanche transistor for limiting the duration of the pulse that is created by said inductor.

16. An apparatus according to claim 14, wherein said emitting means is configured so that the pulse has a fall back period having a fall back rate that is greater than 30 kV/μs.

17. An apparatus according to claim 14, wherein said emitting means is configured so that the pulse has a duration of under 20 ns.

18. A method of performing an ultrasonic investigation of a subject, comprising steps of:

(a) emitting an ultrasonic pulse into a subject, the pulse having a waveform that is shaped by an electrical signal that is generated by a combination of inductive and avalanche elements;

(b) receiving a portion of the ultrasonic pulse that has passed through at least a portion of the subject; and (c) analyzing data that has been received in step (b).

19. A method according to claim 18, wherein step (a) further comprises utilizing an inductor to create a pulse and an avalanche transistor for limiting the pulse that is created by the inductor.

20. A method according to claim 18, wherein step (a) is performed with a pulse that has a fall back period having a fall back rate that is greater than 30 kV/μs.

21. A method according to claim 18, wherein step (a) is further performed with a pulse that has a duration of under 20 ns.

* * * * *